(12) United States Patent
Smith et al.

(10) Patent No.: US 7,801,786 B2
(45) Date of Patent: Sep. 21, 2010

(54) METHOD OF CREATING AND UTILIZING HEALTHCARE RELATED COMMODOTIES

(75) Inventors: Thomas Leonard Smith, Dallas, TX (US); Marshall Howard Hudes, Dallas, TX (US); James Mark Staba, Bradenton, FL (US)

(73) Assignee: Open Market Partners, Inc., Dallas, TX (US)

( * ) Notice: Subject to any disclaimer, the term of this patent is extended or adjusted under 35 U.S.C. 154(b) by 571 days.

(21) Appl. No.: 11/324,031

(22) Filed: Dec. 30, 2005

(65) Prior Publication Data

US 2007/0162367 A1 Jul. 12, 2007

(51) Int. Cl.
*G06Q 99/00* (2006.01)
(52) U.S. Cl. ...................................................... 705/35
(58) Field of Classification Search .............. 705/35–40, 705/2–4
See application file for complete search history.

(56) References Cited

U.S. PATENT DOCUMENTS

| | | | |
|---|---|---|---|
| 5,806,048 A | 9/1998 | Kiron et al. | |
| 6,085,175 A | 7/2000 | Gugel et al. | |
| 6,321,212 B1 | 11/2001 | Lange | |
| 6,546,375 B1 | 4/2003 | Pang et al. | |
| 6,829,589 B1 | 12/2004 | Saliba | |
| 7,254,555 B2 * | 8/2007 | Field | 705/36 R |
| 2004/0143446 A1 | 7/2004 | Lawrence | |
| 2004/0243438 A1 * | 12/2004 | Mintz | 705/2 |
| 2006/0059077 A1 * | 3/2006 | Goodman et al. | 705/37 |
| 2007/0162367 A1 * | 7/2007 | Smith et al. | 705/35 |
| 2008/0015964 A1 * | 1/2008 | Shuster | 705/36 R |

OTHER PUBLICATIONS

"Catastrophe Futures: A Better Hedge for Insurers" Stephen D'Arcy & Virginia Grace France The Journal of Risk and Insurance, 1992, vol. LIX, No. 4.*
www.hedgestreet.com.

* cited by examiner

*Primary Examiner*—Thu-Thao Havan
*Assistant Examiner*—Thomas M Hammond, III
(74) *Attorney, Agent, or Firm*—Ward & Olivo

(57) ABSTRACT

Disclosed are novel tangible financial instruments that allow entities to effectively and efficiently hedge the highly volatile fluctuations associated with predicting healthcare costs and revenues by converting healthcare services into commodities and constructing a financial derivative and a security with an underlying value based on the commodity. The financial instruments create a more efficient marketplace for the exchange of healthcare related products and services.

20 Claims, 8 Drawing Sheets

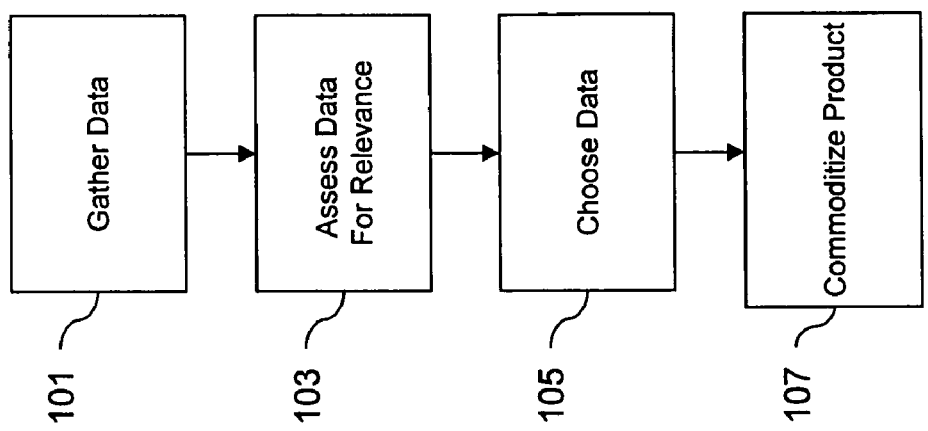

| DRG | Description | Volume | $ / DRG | Annual $ |
|---|---|---|---|---|
| 483 | Tracheostomy w/ mechanical vent 96+ hrs | 100,294 | $ 261,425 | $26.2B |
| 209 | Major joint & limb reattachment procedures of lower extremity | 721,858 | $ 39,970 | $23.8B |
| 127 | Coronary bypass w/ cardiac catheterization | 167,991 | $ 90,630 | $15.2B |
| 373 | Vaginal delivery w/o complications | 2,418,104 | $ 6,239 | $15.1B |
| 14 | Intracranial hemorrhage & stroke w/ infarction | 395,660 | $ 22,940 | $9.1B |
| 79 | Respiratory infections & inflammations age > 17 w/ complications | 252,871 | $ 26,815 | $6.8B |
| 1 | Craniotomy age > 17 w/ complications | 86,476 | $ 75,398 | $6.5B |
| 391 | Normal newborn | 3,085,116 | $ 1,864 | $5.7B |
| 370 | Cesarean section w/ complications | 277,014 | $ 15,519 | $4.3B |

FIG. 2

|  | Total U.S. Procedures | Est. GM Procedures |  | Avg Cost | Total Cost |
|---|---|---|---|---|---|
| DRG 127 (Coronary Bypass) | 168,000 | 733 |  | $ 90,000 | $ 65,978,182 |
| DRG 373 (Vaginal Delivery) | 2,418,000 | 10,551 |  | $ 6,000 | $ 63,307,636 |
| DRG 14 (Brain Hemorrage & Stroke) | 395,000 | 1,724 |  | $ 23,000 | $ 39,643,636 |
| CPT 99213 (Office Visit - 15mins) | 109,000,000 | 475,636 |  | $ 50 | $ 23,781,818 |
| CPT 66984 (Cataract Removal, Lens Insertion) | 3,100,000 | 13,527 |  | $ 675 | $ 9,130,909 |
| CPT 78465 (SPECT (Myocardial) Imaging) | 2,700,000 | 11,782 |  | $ 315 | $ 3,711,273 |
|  |  |  |  |  | $ 205,553,455 |

701 / 703

|  | % of Procedures to "Pre Purchase" | Est. of Purchased Health Care Securities | Anticipated Industry Cost Increase | FMV of 24 month Security** | Initial Outlays |
|---|---|---|---|---|---|
| DRG 127 (Coronary Bypass) | 25% | 183 | 10% | $ 94,500 | $ 17,319,273 |
| DRG 373 (Vaginal Delivery) | 25% | 2,638 | 10% | $ 6,300 | $ 16,618,255 |
| DRG 14 (Brain Hemorrage & Stroke) | 25% | 431 | 10% | $ 24,150 | $ 10,406,455 |
| CPT 99213 (Office Visit - 15mins) | 25% | 118,909 | 10% | $ 53 | $ 6,242,727 |
| CPT 66984 (Cataract Removal, Lens Insertion) | 25% | 3,382 | 10% | $ 709 | $ 2,396,864 |
| CPT 78465 (SPECT (Myocardial) Imaging) | 25% | 2,945 | 10% | $ 331 | $ 974,209 |
|  |  |  |  |  | $ 53,957,782 |

705 / 707

|  |  | Procedures Not Pre Purchased | Actual Cost Increase | Actual Cost/ Procedure | Eventual Outlays |
|---|---|---|---|---|---|
| DRG 127 (Coronary Bypass) |  | 550 | 10% | $ 99,000 | $ 54,432,000 |
| DRG 373 (Vaginal Delivery) |  | 7,913 | 10% | $ 6,600 | $ 52,228,800 |
| DRG 14 (Brain Hemorrage & Stroke) |  | 1,293 | 10% | $ 25,300 | $ 32,706,000 |
| CPT 99213 (Office Visit - 15mins) |  | 356,727 | 10% | $ 55 | $ 19,620,000 |
| CPT 66984 (Cataract Removal, Lens Insertion) |  | 10,145 | 10% | $ 743 | $ 7,533,000 |
| CPT 78465 (SPECT (Myocardial) Imaging) |  | 8,836 | 10% | $ 347 | $ 3,061,800 |
|  |  |  |  |  | $ 169,581,600 |

|  | Total U.S. Procedures | Est. Procedures Performed |  | Avg Cost | Total Cost |
| --- | --- | --- | --- | --- | --- |
| DRG 127 (Coronary Bypass) | 168,000 | 244 |  | $ 90,000 | $ 21,992,727 |
| DRG 373 (Vaginal Delivery) | 2,418,000 | 3,517 |  | $ 6,000 | $ 21,102,545 |
| DRG 14 (Brain Hemorrage & Stroke) | 395,000 | 575 |  | $ 23,000 | $ 13,214,545 |
| CPT 99213 (Office Visit - 15mins) | 109,000,000 | 158,545 |  | $ 50 | $ 7,927,273 |
| CPT 66984 (Cataract Removal, Lens Insertion) | 3,100,000 | 4,509 |  | $ 675 | $ 3,043,636 |
| CPT 78465 (SPECT (Myocardial) Imaging) | 2,700,000 | 3,927 |  | $ 315 | $ 1,237,091 |
|  |  |  |  |  | $ 68,517,818 |

|  | % of Procedures to "Pre Sell" | Est. of Floated Health Care Securities | Anticipated Industry Cost Increase | FMV of 24 month Security** | Initial Inflows |
| --- | --- | --- | --- | --- | --- |
| DRG 127 (Coronary Bypass) | 25% | 61 | 10% | $ 94,500 | $ 5,773,091 |
| DRG 373 (Vaginal Delivery) | 25% | 879 | 10% | $ 6,300 | $ 5,539,418 |
| DRG 14 (Brain Hemorrage & Stroke) | 25% | 144 | 10% | $ 24,150 | $ 3,468,818 |
| CPT 99213 (Office Visit - 15mins) | 25% | 39,636 | 10% | $ 53 | $ 2,080,909 |
| CPT 66984 (Cataract Removal, Lens Insertion) | 25% | 1,127 | 10% | $ 709 | $ 798,955 |
| CPT 78465 (SPECT (Myocardial) Imaging) | 25% | 982 | 10% | $ 331 | $ 324,736 |
|  |  |  |  |  | $ 17,985,927 |

|  |  | Procedures Not Pre Sold | Actual Cost Increase | Actual Price / Procedure | Eventual Inflows |
| --- | --- | --- | --- | --- | --- |
| DRG 127 (Coronary Bypass) |  | 183 | 10% | $ 99,000 | $ 18,144,000 |
| DRG 373 (Vaginal Delivery) |  | 2,638 | 10% | $ 6,600 | $ 17,409,600 |
| DRG 14 (Brain Hemorrage & Stroke) |  | 431 | 10% | $ 25,300 | $ 10,902,000 |
| CPT 99213 (Office Visit - 15mins) |  | 118,909 | 10% | $ 55 | $ 6,540,000 |
| CPT 66984 (Cataract Removal, Lens Insertion) |  | 3,382 | 10% | $ 743 | $ 2,511,000 |
| CPT 78465 (SPECT (Myocardial) Imaging) |  | 2,945 | 10% | $ 347 | $ 1,020,600 |
|  |  |  |  |  | $ 56,527,200 |

FIG. 8

METHOD OF CREATING AND UTILIZING HEALTHCARE RELATED COMMODOTIES

FIELD OF THE INVENTION

The present invention generally relates to the fields of healthcare and finance. More specifically, the present invention relates to the creation of healthcare related commodities in the form of financial derivatives and securities. Such healthcare related commodities can be utilized to manage the risks associated with unreliable healthcare costs and create an efficient marketplace for healthcare services and products.

BACKGROUND OF THE INVENTION

An issue that is the subject of intense debate among academics and financial professionals is the Efficient Market Hypothesis ("EMH"). The hypothesis states that the price of a security is an accurate reflection of all available information.

Individuals, corporations, and other entities purchase securities and derivatives under the assumption that the securities they purchase are worth more than the price that they are paying. Similarly, sellers of derivatives and securities assume that the services they are selling are worth less than the selling price. However, if markets were completely efficient and contemporaneous prices fully reflected all information available, then outperforming the market would become a matter of happenstance. As a result, if a market could be completely efficient, there would be no information or analysis that could result in over-performance of an expected benchmark.

A completely efficient market would be a market in which rational, profit-oriented entities compete and try to predict future market values of individual securities and derivatives. Information would be freely available to all participants. In an efficient market, competition between entities would result in a situation where actual prices of individual securities and financial derivatives would already reflect the effects of events that have occurred. In addition, prices would reflect events which are expected to take place in the future. In short, an efficient market would allow an entity to know the actual value of a security or other financial instrument at any point in time.

There are three forms of the Efficient Market Hypothesis: the weak form, the semi-strong form, and the strong form. The weak form assumes that all past market prices and data are fully reflected in financial derivative securities prices. In other words, technical analysis is unnecessary because market price already reflects that which can be analyzed from a technical standpoint. The semi-strong form assumes that all publicly available information would be fully reflected in securities prices. In other words, fundamental analysis would be of no use because the information utilized in such an analysis would already be incorporated into the price. The strong form assumes that all information is fully reflected in securities prices. In other words, even insider information would be of no use (i.e., insider information would already be incorporated into the price of a commodity.)

In practice, markets are neither perfectly efficient nor completely inefficient. All markets are efficient to a certain degree, and some are more efficient than others. In markets with substantially low efficiency, more knowledgeable investors can often outperform less knowledgeable investors. For example, government bond markets are considered to be extremely efficient. Most researchers consider large capitalization stocks to also be very efficient, while small capitalization stocks and international stocks are considered by some to be less efficient. Real estate markets and venture capital markets, which do not have fluid or continuous markets, are generally considered to be less efficient because different participants may have varying amounts and quality of information. In addition, many markets are flooded with thousands of intelligent, well-paid, and hard-working investors seeking under and over-valued securities to buy and sell. Efficiency of a market is largely dependent on the number of participants and the rate of dissemination of information.

Efficiency of markets plays an important role in the decision to invest. Because more efficient markets more accurately reflect available information, prices are relatively stable and reliable. As a result, entities can offer various securities and derivatives which have a value based on the underlying stable prices. For example, bond markets and stock markets are well known markets having relatively stable prices. Conversely, markets that are considered inefficient such as the real estate market and various venture capital markets are more speculative in nature. As such, underlying prices may be very unstable. Accordingly, established derivative and securities markets are lacking.

An established market utilizes a variety of financial instruments. These instruments are used for a variety of purposes, from investing in a given stock to hedging risks wherein parties exchange derivative instruments in order to offset the price risk associated with fluctuations in cash markets.

Many entities including commercial firms, consumers, and producers utilize hedging techniques to protect against price risk. Hedging enables a party to transfer risk to another party because the parties leverage related products and services which respond similarly to the same economic factors. This leverage of related products and/or services is known as correlation.

An entity can use any of several derivatives for these purposes. The simplest of such derivatives is known as a forward contract, which is a transaction wherein a buyer and a seller agree upon price and quantity for delivery of a specific service or commodity at a future point in time. Forward contracts are not standardized, so each transaction must be negotiated individually. In addition, while such forward contracts are legally binding, upon default a party must resort to the legal system for recovery. Accordingly, transaction costs associated with negotiating, maintaining and enforcing forward contracts are often unnecessarily high.

Of course, these contracts can be standardized as to include specific terms. Standardized forward contracts or futures contracts are generally standardized with respect to quantity, time, and place for delivery of goods and services. Because futures contracts are standardized, an entity can theoretically purchase and sell futures contracts without ever actually taking physical delivery of the subject of the contract.

To eliminate the need for legal enforcement of a forward contract, a margin system was created to prevent buyers and sellers from defaulting on their contract. In a margin system, the buyer and the seller of a futures contract deposit cash to a margin account maintained by a third party, usually an exchange or a bank, as collateral to guarantee performance of the futures contract. In addition, a margin may be "marked-to-market," whereby the amount of money deposited into a margin account is updated continuously as the price of the underlying derivative fluctuates.

Since the terms of a futures contract are standardized and delivery need not ever be completed, a properly executed contract is all that is required for buying, selling, and trading the contract, making the process fairly liquid. To improve the liquidity of this process, exchanges were formed to facilitate these transactions on a larger scale. Currently, exchanges are the preferred forum for trading futures contracts because risk managers appreciate the benefits of standardized features.

Futures options are analogous to futures contracts. The difference between the two is the fact that with futures options a party is not actually obliged to actually accept delivery of the underlying commodity. Instead, a party has the right to refuse delivery. The result is that unlike futures contracts, futures options are not subject to margin calls (i.e., the instrument is not marked to market unless a party actually takes delivery) and have lower potential risk. There are disadvantages to purchasing a futures option. For example, because one party has the right to refuse delivery of the futures option, the futures option is more expensive to purchase that a futures contract. The higher price negatively impacts the return of the instrument, resulting in a lower yield. Because the yield is lower, it is a more inefficient risk management tool than a standardized futures contract.

As an example, consider a wheat farmer who wishes to sell his upcoming harvest. While prices for his crop remain steady, the farmer is worried that the value of his crops at harvest time will drop. The farmer (seller) can agree to deliver his wheat at harvest time to a miller, (buyer), who is worried that the price of wheat will increase between the contract date and the harvest (delivery) date. The farmer and the miller have both attempted to manage the risk of the commodity, namely wheat. Note that if the price of wheat rises, the miller is said to gain value because the contract was executed at a lower price. Conversely, if the price of wheat falls, the farmer gains value because the contract was executed at a premium over the price the farmer could have obtained.

The same principles hold for intangible financial products and services. For example, consider an entity that holds a contract to sell a product in a foreign market that will be paid for in foreign currency. If the foreign currency increases in value relative to the domestic currency, it will convert into less domestic currency. To protect itself against this currency risk, the domestic entity can buy a foreign currency futures contract. Similar to the farmer/miller example, if the foreign currency appreciates, the loss on conversion on the initial contract is offset by the increased value of the futures contract.

In addition, efficient markets allow investors and other entities to buy and sell financial instruments known as securities. A security is a type of transferable interest representing financial value. There are two general classes: debt securities and equity securities. Both types are represented by a certificate. For example, shares of corporate stock, bonds issued by corporations or governmental agencies, and mutual funds are all examples of securities.

Issuers (i.e., sellers) of securities include commercial companies, government agencies, local authorities and international and organizations. Debt securities issued by government generally carry a lower interest rate than corporate debt issued by commercial companies.

Entities typically utilize securities to raise new capital because they are an attractive option relative to bank loans which tend to be relatively expensive and short term. Through securities, capital is provided by investors who purchase the securities. In a similar way, a government can raise capital from securities if taxation and other income are insufficient to meet public expenditure.

Investors (i.e., purchasers) include investment banks, insurance companies, pension funds, individuals, and other corporations. Investors purchase securities to receive income and/or achieve capital gains.

The holder of a debt security is owed a debt by the issuer and is entitled to the payment of principal and interest, together with other personal rights under the terms of the issue, such as the right to receive certain information. Debt securities are generally issued for a fixed term and are redeemable by the issuer at the end of that term. They generally offer a higher rate of interest than bank deposits.

Another example of a debt security is a treasury bond, which is a medium or long term debt security issued by a government. It typically carries lower interest rates than corporate bonds (i.e., they offer less yield). In addition, money market instruments such as certificates of deposit and commercial paper are classified as securities. They are short term, highly liquid, and offer low interest rates.

An equity derivative, in contrast, is typically considered to be an ordinary share in a company. The principal advantage of equity is the prospect of capital growth.

Securities markets are divided into primary markets and secondary markets. Primary markets (also known as capital markets) are comprised of new securities to their first holders (e.g., an Initial Public Offering). Issuers usually retain investment banks to assist them in finding buyers for these issues, and in many cases, to buy any remaining interests themselves. This arrangement is known as underwriting.

Transferability is an essential characteristic of securities. Transferring, or trading of these securities is done on the secondary market. Secondary markets are often referred to as stock exchanges. The value of securities sold on exchanges is determined by the number of willing buyers and sellers (i.e., the market determines their value). As a result, efficient capital markets are vital to their success.

Efficient capital markets allow entities to better hedge their risk. However, entities do not hedge against every contingency. If the risk that needs to be hedged has only a small impact on an entity's bottom line, it may decide that hedging against that risk is unnecessary. Accordingly, an entity typically only hedges large expenditures and/or commodities that substantially impact the bottom line due to their underlying volatility.

For example, consider an entity that has a large exposure to inflation. To manage this risk the entity can purchase and/or trade a Consumer Price Index (CPI) future. The CPI index is a measure of inflation based on publicly available information. Since almost every entity is exposed to inflation related price risk there is a large market for buyers and sellers who wish to manage this risk and the CPI index market trades at a high volume. While it can be generally utilized effectively to hedge short-term changes in inflation, and the index price is stable because it is based on government-published historic data, it is a new type of futures contract. As such, the total number of contracts available is limited. In addition, the CPI index is not an accurate measure of the volatility of uncorrelated products and services (e.g., healthcare) because uncorrelated products and services increase in price at a different rate than inflation.

By way of example, healthcare costs in the United States are presently increasing at two to three times the rate of inflation and at four times the rate of wage increases. In an attempt to measure the increase in healthcare costs, entities rely on the healthcare trend, which indicates the percentage increase of healthcare expenditures per capita over a predetermined period of time. The components of the healthcare trend are highly variable, making the healthcare trend extremely volatile. Therefore entities that attempt to manage health related expenditures have difficulty budgeting and forecasting these costs due to this volatility, which affects the entity's bottom line. Because of the direct impact of sharply rising healthcare costs on an entity's financial stability, managing the price risk of healthcare related costs is vital.

For example, a Fortune 100 company like General Motors has high financial exposure to such risk factors as currency risk, credit risk from its financing division, interest rate risk from its financing division, and fuel cost risk from the sale of automobiles. These financial risks are correlated to significant sources of revenue from (or significant expenditures related to), automobile products and services. General Motors therefore hedges against these risks in one form or another by utilizing financial derivative instruments.

In 2003, General Motors (GM) spent $4.8 billion on healthcare for its employees, which constituted an expenditure greater that its expenditure for steel. Because healthcare costs comprise a large percentage of General Motor's expenditures, one would expect it to manage its healthcare risk by utilizing financial derivatives.

However, no such market exists. There is no market for tangible financial derivatives because the healthcare industry is extremely inefficient. Rather than allow the traditional market forces of supply and demand to dictate the price of providing healthcare, a "command and control" system is utilized for managing healthcare expenditures. As a result, corporations such as General Motors must utilize more traditional healthcare management techniques to control the costs associated with providing healthcare.

Cost management techniques include health insurance, alternative procurement strategies, on-site medical facilities, employer network creation, and lifestyle/wellness management programs. Further, corporations often alter existing health insurance plans by making benefit adjustments, imposing access restrictions, altering eligibility requirements, and creating alternative healthcare plans.

Insurance premiums associated with such insurance have been rising at an alarming rate due to increasing costs that reflect the inherent variability of the healthcare industry, such as the cost of prescription drugs. In addition, insurance premiums are inflated, for example, by transaction costs related to contract maintenance and contract negotiations. Similarly, administration of these plans is extremely costly because plans are not standardized (i.e., they are corporation specific). As a result, the present system for managing risk associated with healthcare costs (i.e., health insurance) is inefficient.

As premium costs continue to rise, insurance companies presently offer a variety of insurance types in an attempt to manage price risk and volatility of healthcare expenditures.

One type of the insurance now offered is a method of reducing healthcare costs known as stop-loss insurance.

Stop-loss insurance can be purchased by self insured employers in an attempt to stabilize their healthcare costs. While a typical self insured employer can predict the approximate number of doctor visits its employees will have in a given year, it cannot predict the number of "catastrophic events" (e.g., premature births, cancer, and organ transplants) that will occur in a given year. The costs associated with these procedures can be devastatingly high to a self insurer so there is a need to hedge against this type of risk.

There are two main types of stop-loss insurance. The first is known as Individual Stop Loss "ISL," sometimes called Specific Stop Loss. Individual Stop Loss protects an employer against large claims incurred by an individual employee or dependent which exceed a predetermined dollar limit chosen by the employer. For example, if an employee of the insured incurs injuries in an accident that requires expenditures that far exceed the policy's stated deductible, the ISL insurance would reimburse the employer for all associated expenses beyond a predetermined dollar amount.

The second type of stop-loss insurance is known as Aggregate Stop Loss (ASL), or Excess Risk Insurance. Aggregate Stop loss insures an employer against the total expenditures by its employees as compared to a predetermined dollar amount. An employer typically purchases ASL to cover against 125% of the level of expected claims predicted by the insurance carrier. For example, a mid sized self insurer with $4 million in expected claims could purchase a stop loss policy that initiates when $5 million in claims are incurred.

Despite the obvious advantages associated with the various types of stop loss insurance, there are numerous disadvantages. For example, conservative pricing and limited availability of stop loss insurance policies severely curtails the usefulness of stop loss insurance to small health plans with limited financial resources. In contrast, large companies can afford the costs associated with a few catastrophic claims, so the steep cost of stop loss insurance becomes economically wasteful.

In addition, like traditional insurance, stop loss premiums are inflated, for example, by transaction costs related to contract maintenance and contract negotiations, as well as costly administrative expenses.

Consequently, stop loss insurance is limited to mid-sized self insured employers because such entities often do not have large enough cash reserves or generate enough income to cover the costs associated with several catastrophic claims. In addition, stop loss insurance solutions only maintain extreme volatility because typical stop loss plans do not take effect until the incurred claims exceed a 25% threshold. Thus, current insurance practice is highly inefficient.

The current process of determining pricing associated with healthcare is extremely inefficient. Currently, the government determines public healthcare prices utilizing the Resource Based Relative Value Scale (RBRVS).

The RBRVS is published annually by the government as a component of the Medicare Physician Fee Schedule by the Center for Medicare and Medicaid Services (CMMS). In short, the RBRVS assigns a relative value to individual medical procedures and services based on the government's determination of the complexity of the procedure or service, rather than the market value of such a procedure. By way of example, the current relative value for an initial office visit is 0.97, while the relative value of a heart transplant is 98.59.

To determine the suggested retail price of a procedure or service, the relative value is multiplied by a physician's conversion factor (e.g., $100.00) and modified by a series of multipliers which purport to account for regional variability. These factors include the Geographic Cost of Practice Index (GCPI) and the Geographic Adjustment Factor (GAF). The GCPI attempts to take into account factors such as geographic practice expenses and medical malpractice insurance expenses. For example, the practice expense multiplier in San Francisco is 1.501, while the multiplier for South Dakota is 0.365.

The GAF is purports to more accurately reflect fees for associated with a specific city, county, area, region and state. As an example, the GAF multiplier for Detroit is 1.610, while the GAF for South Dakota is 0.747.

Therefore, to achieve the final value of any particular medical procedure or service in a particular region, the RBRVS for that procedure of service is multiplied by a conversion factor, GCPI and GAF.

As a result, the government attempts to set RBRVS values using formulas and statistics as opposed to natural supply and demand. This process is inherently inefficient because the government necessarily sets higher values for some services and lower values for others than would be established through supply and demand dynamics. This inefficiency is further compounded by the need for multiple geographic factors.

Since most private healthcare payers utilize the government's methodology as the basis for contract negotiations with providers, the process perpetuates and magnifies the valuation problem.

Additional market inefficiencies exist in regards to private healthcare providers. Currently, private providers negotiate with each healthcare provider individually, thereby increasing transaction costs such as legal fees and wasting limited financial resources. Further, subjective factors such as the reputation of a party, personal connections between negotiators, and previously agreed upon pricing are utilized to determine the price of healthcare for a given contract. This negotiation process leads to the proliferation of asymmetric information, negatively influencing the efficiency of any potential market. As a result, the cost to provide healthcare is inordinately high and volatile.

Because there are no healthcare risk management techniques which utilize tangible financial derivatives to control escalating healthcare costs, there is a clear need in the art for a tangible financial instrument which is capable of being traded in an efficient market. The present invention overcomes the various deficiencies associated with this shortcoming by creating a novel tangible financial instrument in the form of a derivative contract or a security product that allows entities to effectively and efficiently hedge the highly volatile fluctuations associated with predicting healthcare costs by converting healthcare products and services into commodities and constructing a financial instrument with an underlying value based on the commodity.

SUMMARY OF THE INVENTION

Disclosed is a method for commoditizing a healthcare related products, procedures, and services. In general, the method entails gathering a source of data, assessing it for relevance to overall medical procedures and/or services, and creating a commodity based on the relevant data. Any source of data can be used, but it needs to define the medical services, procedures, and products in such a way as it is agreeable to both buyers and sellers in the proposed market. It has been discovered that some medical codes are currently utilized by market participants in the healthcare industry can be used to determine how services, products, and procedures are exchanged for money. Accordingly, these codes can be utilized to construct a related financial instrument.

Medical codes are well known in the healthcare industry; therefore, a further explanation is not warranted, but it should be noted that all existing and/or future developed medical codes can be utilized with the present invention. By way of non-limiting examples, the following codes correlate with the market value of medical procedures and services: Ambulatory Surgical Center (ASC), Ambulatory Payment Classifications (APC), Current Dental Terminology (CDT), Code on Dental Procedures and Nomenclature (CDPN), Current Procedural Terminology (CPT), Diagnosis Related Grouping (DRG), Episode Treatment Groups (ETG), Health Care Financing Administration Common Procedure Coding System (HCPCS), International Classification of Diseases (ICD-9,ICD-10), National Drug Codes (NDC), Revenue Codes, and Per Diems. Of course, any data source that could be used as an agreed upon definition of services and/or products by both buyers and sellers can be utilized in accordance with the present invention without departing from the spirit of the invention.

Currently, the method of the present invention assesses the relevance of the code source to evaluate whether it can be commoditized. Factors included in relevance determinations include but are not limited to payment and contract usage, public and private usage, minimal functional overlap, general acceptability, reliability, consistency, independence, and neutrality.

Finally, the code source is used to create a tangible commodity that can be traded via a financial instrument.

Once such a financial instrument exists, it can attract a large market for buyers and sellers of the instrument as a method of managing both costs and risk. For example, typical buyers would generally comprise entities which currently provide healthcare insurance related services and can be self insured employers, entities with large or mid-sized health plans, workers compensation insurers, re-insurers, the United States and/or foreign governments, local governments, state governments, and speculators. Typical sellers would generally comprise entities which provide healthcare services and could include hospital systems, pharmaceutical companies, medical supply companies, healthcare sector mutual fund companies, physician groups, re-insurers, and speculators. Of course, other parties could purchase healthcare related financial instruments as well.

A healthcare related financial instrument is created such that price of the instrument correlates to the price of the underlying commodity.

The healthcare related financial instruments can be traded on a publicly available exchange, such as the Chicago Board Options Exchange, over the counter, or on a private exchange. Benefits associated with trading the financial derivative of the present invention on an exchange include improved liquidity and increased volume.

Also disclosed is a method of utilizing tangible financial commodities to create various portfolios of holdings commonly known in the art as "baskets."

The financial instruments can be any financial derivative known to one of ordinary skill in the art, such as a futures contract, a forward contract, a debt obligation, a security, a futures option, or any new financial instrument developed in the future. The price of the instrument is related to the commodity because each instrument represents a tangible procedure or service. By using an instrument with standardized features such as quantity and delivery date, the instrument can then be treated as a commodity, tradable on an exchange.

The present invention also discloses a method for using the associated instrument to hedge the risk associated with healthcare costs. To accomplish this, an entity creates a hedge ratio to determine the number of derivatives to purchase in order to mitigate a deviation in predicted healthcare related prices. After determining the hedge ratio, an entity can buy or sell the appropriate instruments.

Also disclosed is the creation of a security product similar to a debt offering which is based on a tangible healthcare related commodity. Essentially, individual hospitals or healthcare providers can offer collateralized contracts for a percentage of their overall capacity for one or more medical services or procedures (e.g., for 50% of their coronary bypass procedure capacity). Because the contracts are offered on an individual basis for an agreed upon service which is performed at an agreed upon facility(ies) within an agreed upon timeframe at a predetermined rate of return (i.e., like a coupon bond), geographical differences and quality of procedure differences are intrinsically accounted for, enhancing the efficiency of the market. In addition, the offering is underwritten as in a traditional manner, reducing any credit risk associated with it. Since hospitals currently issue bonds, they are already rated by firms such as Moody's, so the value and reliability is easily ascertained.

Such an offering of collateralized contracts can benefit both buyers and sellers. For example, traditional sellers of such securities get much needed revenue upon execution of the transaction, in exchange for a promise to perform future medical services or procedures at a predetermined price. Therefore the seller receives cash upfront and the buyer receives future price certainty. In addition, both buyers and sellers improve their cost of capital since the offering takes advantage of the intrinsic spread between a large buyer's low cost of capital and a healthcare provider's large borrowing cost.

Accordingly, an object of the present invention is to provide a system and method which enables an entity to hedge risk associated with healthcare expenditures.

Still another object of the present invention is to improve the efficiency of the healthcare services and products market.

Another object of the present invention is to utilize publicly available data to create a tangible medical commodity.

Still another object of the present invention is the creation of a financial derivative having a price determined by an underlying healthcare related commodity.

Yet another object of the present invention is to create a standardized healthcare related financial derivative instrument.

Another object of the present invention is the creation of a financial security having a price determined by an underlying healthcare related commodity.

Another object of the present invention is to create an efficient market to exchange a healthcare related commodity.

It is another object of the present invention to create an instrument that is available for purchase over the counter.

Still another object of the present invention is to create a medical commodity that can be traded in an efficient market having stable prices.

Yet another object of the present invention is to create a tangible medical commodity which accurately reflects the market value of the associated medical procedure.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

FIG. 1 is a flow chart generally depicting the method of creating a commodity from a medical procedure.

FIG. 2 is a tabular depiction of several of the component parts of a preferred data source.

FIG. 7 depicts the calculation of values necessary for a self insuring company to purchase a security product in accordance with the present invention.

FIG. 8 depicts the calculation of values necessary for a healthcare provider to sell a security product in accordance with the present invention.

DETAILED DESCRIPTION OF THE PREFERRED EMBODIMENT

Figure 3:
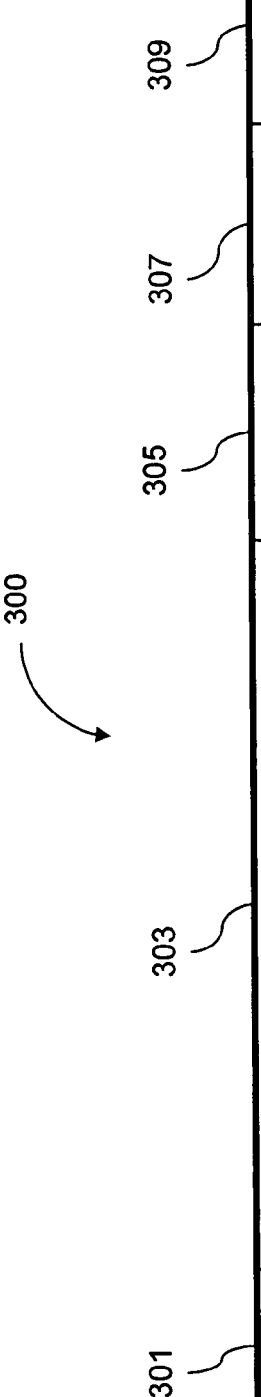
FIG. 3 is a tabular depiction of several of the component parts of another data source.

A detailed illustrative embodiment of the present invention is disclosed herein. However, techniques, systems and operating structures in accordance with the present invention may be embodied in a wide variety of forms and modes, some of which may be quite different form those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

Moreover, well known methods, procedures, and substances for both carrying out the objectives of the present invention and illustrating the preferred embodiment are incorporated herein but have not been described in detail as not to unnecessarily obscure novel aspects of the present invention.

None of the terms used herein, including "future", "futures contract", "derivative", "instrument", and "option" are meant to limit the application of the invention. The terms are used interchangeably for convenience and are not intended to limit the scope of the invention. Similarly, the use of the term "company" or "corporation" is not meant to limit the scope of the invention to one type of entity, as any entity or individual can also utilize the present invention. The following presents a detailed description of a preferred embodiment of the present invention.

Referring to FIG. 1, depicted is a method of commoditizing a medical procedure and/or service as shown in step 107. Initially, data related to healthcare can be gathered 101 from any source as depicted in step 101. In a preferred embodiment this data is made available periodically from a public source and has proven to be credible, reliable, and frequently disseminated. The data source according to the preferred embodiment is data related to healthcare codes for reasons discussed below. An ordinarily skilled artisan would recognize that any data source can be utilized including: Ambulatory Surgical Center (ASC), Ambulatory Payment Classifications (APC), Current Dental Terminology (CDT), Code on Dental Procedures and Nomenclature (CDPN), Current Procedural Terminology (CPT), Diagnosis Related Grouping (DRG), Episode Treatment Groups (ETG), Health Care Financing Administration Common Procedure Coding System (HCPCS), International Classification of Diseases (ICD-9), International Classification of Diseases (ICD-10), National Drug Codes (NDC), Revenue Codes, and Per Diems. In the preferred embodiment of the present invention, the data is downloaded from an online source (e.g., the internet) and stored in a database, but any well known method of gathering data can be utilized to gather the data as depicted in step 101 without departing from the spirit of the invention.

According to the present invention, after data is gathered in step 101, the data is assessed and filtered with respect to its relevance as depicted in step 103 by comparing the data to healthcare related economic factors. In the preferred embodiment of the present invention, the data is assessed according to one or more criteria including but not limited to: payment and contracting usage, public usage, private usage, minimal functional overlap, general applicability, general acceptability, reliability, consistency, independence, neutrality, relevance, timeliness, understandability, and market applicability of the data. Any method and means for assessing and categorizing the data can be used without departing from the scope of the invention. It is contemplated that any number of factors can be cited, and any subjective ranking system can be implemented in accordance with the present invention.

It has been discovered that certain medical codes can be utilized as potential data sources. These codes, which can relate to billing or other aspects of medical procedures, are well known in the healthcare industry and are currently utilized for insurance repayment. Advantageously, these codes have predefined descriptors outlining the specifications of any given medical procedure. As a result, the codes contain pre-divided, discrete, subsets of data relating to medical procedures. This allows the codes to be used for a multitude of medical procedures. In addition, it is contemplated that new code identifiers will be created as new medical procedures and services are developed. These new codes can be utilized in accordance with the present invention.

The discrete codes from the data source are correlated to the total number of procedures performed per time period to determine whether a potential market for a commodity can be developed. In the preferred embodiment, the time period is one year, however, any time period can be used. The average cost per procedure is then correlated to the discrete procedure, as shown in FIGS. 2-3.

Referring to FIG. 2, shown are discrete medical procedure codes 201 and the description 203 as defined by data source 200. In this example, data source 200 is derived from the Diagnosis Related Grouping codes ("DRG"). The number of procedures 205 and the average cost per procedure 207 are correlated. In the present example, the correlation relates to projected total potential market for a commodity. In addition, as will be described in greater detail below, cost per procedure 207 can be utilized to create the price for a financial instrument.

Similarly, FIG. 3 shows several discrete medical procedure codes 301 and the description 303 as defined by data source 300. In this example, data source 300 is derived from the Current Procedural Terminology ("CPT") codes. The number of procedures 305 and the average cost per procedure 307 are correlated. In the present example, the correlation relates to projected total potential market for a commodity. Again, as will be described in greater detail below, cost per procedure 307 can be utilized to create the price for a financial instrument. Of course, any other data source or code source can be utilized in accordance with the present invention.

Referring again to FIG. 1, a data source is chosen as depicted in step 105 after assessing the data source for relevance 103. In accordance with the preferred embodiment of present invention, a data source that correlates with the preferences of buyers and sellers (i.e., potential market sizes 209 and 309 as depicted in FIGS. 2-3) is selected.

Once a data source is chosen as shown in step 105, a medical procedure is commoditized and generated as depicted in step 107. By correlating the average price for a given procedure as defined in a data source (e.g., DRG or CDT), an initial value for a procedure can be determined. Advantageously, buyers and sellers can use this price to gauge the value of any given medical procedure. Basic well known market mechanisms of supply and demand then shift the price accordingly. For example, the current average nationwide price for a coronary bypass as defined by the DRG is approximately $90,000. Any contract or offer for sale that is at that price will induce an entity that currently pays more than that amount for a coronary bypass (i.e., more than $90,000) to purchase it. In short, the entity becomes a willing buyer. Similarly, a hospital or healthcare provider that currently charges less than the average price for a coronary bypass (i.e., it charges less than $90,000 for the procedure) will become a willing seller of the procedure at that price. As a result, normal economic market forces convert the medical procedure into a tradable, easily convertible, commodity with properties similar to known commodities such as oil or wheat. However, in order to fully exploit the commoditization of the medical procedure, an underlying contract must be formed. In accordance with the present invention, the underlying contract is a financial instrument.

A preferred method of utilizing the commoditized medical procedure of the present invention is to construct a financial instrument that utilizes the underlying commodity as a price source. Typical instruments include derivative instruments such as futures contracts and futures options, as well as other types of derivatives well known in the art. In addition, securities can be constructed in accordance with the present invention. In the preferred embodiment of the present invention, the derivative instrument utilized is a futures contract comprised of a forward pricing contract with a settlement price determined by the underlying medical commodity and other standardized features. In alternative embodiments of the present invention, other financial derivative instruments (e.g., a futures option contract) can be utilized as well.

Although the purchase date and settlement date of the derivative can be any date, in the preferred embodiment of the present invention, the financial derivative settlement date corresponds with the projected medical procedure costs for a given time period. In addition, it is preferred that the settlement date of the financial instrument corresponds to the same period of the buyer's and seller's underlying projected capacity for the given medical product, procedure, or service.

Formulating a futures contract in such a manner minimizes arbitrage opportunities and improves efficiency in trading markets because it ensures that every party receives the information at the same time. That is, it eliminates the problem of asymmetric market information.

In the preferred embodiment of the present invention, the derivative is created having standardized features such that it can be offered on an existing exchange. For example, a standardized futures contract is typically a forward pricing contract purchased on a margin that is assessed daily. In addition, they are marked to market and have standard settlement dates.

Of course, there may be incremental margin requirements incurred with the trading of this instrument. The exact amount initially depends on the exchange, the type of futures contract, and the instrument's volatility. In addition, for the purposes of the foregoing examples, brokerage fees are estimated to be approximately $10 per contract.

While offering the contract on an exchange does require purchasing it on margin, most entities already have a margin account at the larger exchanges, so that this requirement will have little, if any impact on cash flow.

It is not necessary for the derivative instrument described in the preferred embodiment of the present invention to be offered on an exchange. Rather, it is contemplated that alternative embodiments of the present invention can include unique derivative instruments offered "over the counter."

These alternatives allow for customization of financial derivatives, including the creation of a basket of derivatives.

The present invention further relates to a method of using a financial derivative to manage the risks associated with healthcare volatility.

Figure 4:
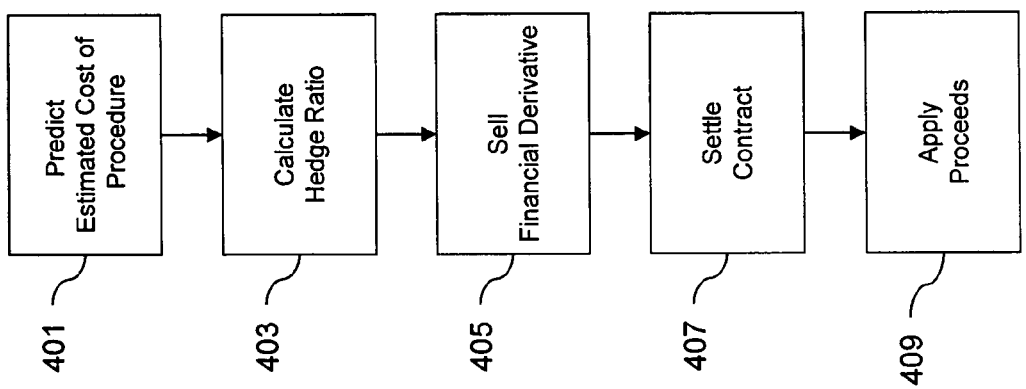
FIG. 4 is a flow chart depicting a method in which a large company can hedge against healthcare volatility by purchasing a tangible medical commodity financial derivative.

Referring now to FIG. 4, shown is an example of a self insured employer utilizing a financial derivative based on a tangible medical commodity to manage its risk against healthcare cost volatility in accordance with the present invention. Initially, an entity predicts the expected number of a certain medical procedure as depicted in step 401. Any means of predicting the expected number of procedures can be used, all of which are well known in the art. The preferred embodiment of the present invention will be demonstrated by an example in which a Company predicts that it will incur $60 million in coronary bypass claims as defined by DRG code 127 (i.e., a coronary bypass procedure). In addition, the cost of a coronary bypass procedure is projected to increase 10%, from $90,000 to $99,000. The Company also predicts that in its worst-case scenario, the costs incurred will be $9 million higher than originally predicted (i.e., the worst case scenario assumes that actual claims incurred will be 15% higher than expected). Conversely, the Company predicts its best-case scenario to be that its costs incurred are $3 million less than predicted (i.e., the best case scenario assumes that actual claims incurred will be 5% less than expected).

After predicting its costs, the Company determines the appropriate number of futures contracts to sell in order to effectively hedge against the calculated risk associated with the prediction of step 401. To accomplish this, the Company calculates hedge ratio 403 using the price of contemporaneously available futures contracts based on the underlying coronary bypass procedure (i.e., DRG 127). In this example, it is assumed that contemporaneous futures contracts are selling at $90, which reflects a 10% increase in the cost of a coronary bypass procedure over the course of the year. Using this data as a starting point, the Company decides how much risk exposure they wish to hedge against and how much of their cash holdings they will spend to hedge that exposure. These factors are combined to form a hedge ratio in any known manner. Indeed, today many entities either calculate their own hedge ratios with respect to non-healthcare risk or rely on consulting firms to help determine such hedge ratios. Of course, other embodiments of the present invention allow for various other factors to be incorporated into a hedge ratio, as is well known in the art. The hedge ratio is then utilized by the Company to calculate the number of contracts to sell.

After determining the number of contracts to sell, the Company sells the requisite number of contracts in step 405. In the preferred embodiment of the present invention, the Company determines that it will sell 60 contracts at $90.00 per contract. The Company can either construct custom futures contracts in the manner previously described or use a standardized futures contract, and we assume the quantity of each standardized contract is 10,000.

In accordance with the present invention, the Company can then offer the futures contracts for sale privately, over the counter, or publicly on an exchange. In the presently described preferred embodiment, the contracts are offered on an exchange, but in alternative embodiments, the contracts could be standardized and offered on an exchange or the Company could construct the contracts in any manner that it chooses and offer them for sale in any manner.

After offering the contacts for sale, the Company can allow the contracts to settle as shown in step 407. Alternatively, it can manage the futures contracts in any known manner, including repurchasing any portion of the contracts it has offered on any day at a value determined by the commodity price, or selling more contracts at the market price.

On the settlement date of the futures contracts, the Company delivers its contracts. The value of the commodity on the settlement date is used to determine the settlement price. In the preferred embodiment, it is assumed that on the settlement date the price of an actual coronary bypass increased to $103,500. The contract value is then determined by the following formula:

$$100-(100*((\text{Commodity Price on settlement date}/\text{Commodity Price on offer date})-1))$$

Knowing that the cost of a coronary bypass is $103,500 at settlement and that the cost of a bypass at offering was $90,000, the contract value is calculated as $85.00.

To determine its total profit or loss, the Company uses the formula:

$$\text{\# Units/contract}*\text{\# of contracts}*\text{price difference}=\text{Profit (Loss)}$$

In the presently described embodiment the Company would profit in the amount $3,000,000.

Note that when implementing the formula, the number of contracts is expressed as a negative number to indicate that the Company sold them (i.e., if the Company had purchased the contracts, the value would be reflected as a positive number).

In the presently described embodiment, it is assumed that the cost of a coronary bypass rose above the expected threshold of 10%. The actual percentage increase can be determined by using the below formula:

$$((\text{Commodity Value at Settlement}-\text{Commodity Value at Offering})/\text{Commodity Value at offering}))*100\%$$

In the presently described embodiment, the cost of a coronary bypass rose 15.00%. Because the volatility of coronary bypass costs was higher than expected, the Company's yearly predictions were too low (i.e., the worst case scenario occurred). Accordingly, the Company's actual expenses are assumed to be $69 million. To properly hedge against its erroneous predictions, the Company applies the proceeds 409 from the sale of the contracts (e.g., $3,000,000) to the increased cost of healthcare. In the presently described embodiment, the Company has a net loss of zero, the difference between the increase in predicted healthcare costs above management's pro form a statement and the monies earned on the futures contract. In this example, the Company has perfectly hedged against the increased costs of multiple coronary bypass procedures. Of course, perfect hedging rarely occurs and this example assumes that transaction costs are negligible. Note however, that without hedging in accordance with the present invention, the Company would have incurred a profit/loss variance of $3,000,000.

Table 1 illustrates the benefits to the Company of hedging risk utilizing a financial derivative based on the tangible medical commodity in accordance with the present invention:

TABLE 1

Risk Management Comparison

| Company<br>1. Budget Projection | Base Case<br>No Hedge | Stop-Loss | Futures |
|---|---|---|---|
| Claims Incurred 2004<br>(in $millions) | 60.0 | 60.0 | 60.0 |
| Expected Trend | 10% | 10% | 10% |

TABLE 1-continued

Risk Management Comparison

| | | | |
|---|---|---|---|
| 2004-2005 | | | |
| Expected Claims 2005 | 66.0 | 66.0 | 66.0 |
| Net Expected (Excluding any reimbursement or cost from hedge) | 66.0 | 66.0 | 66.0 |

| | Low Trend | High Trend | Low Trend | High Trend | Low Trend | High Trend |
|---|---|---|---|---|---|---|
| 2. Actual Experience | | | | | | |
| Actual Trend 2004-2005 | 5% | 15% | 5% | 15% | 5% | 15% |
| Actual Claims 2005 (in $millions) | 63.0 | 69.0 | 63.0 | 69.0 | 63.0 | 69.0 |
| Cost of Hedge | N/A | N/A | 1.0 | 1.0 | N/A | N/A |
| Settlement of Hedge | N/A | N/A | 0.0 | (1.5) | 3.0 | (3.0) |
| Net Expenses | 63.0 | 69.0 | 64.0 | 68.5 | 66.0 | 66.0 |
| 3. Difference From Expected (in $millions) | (3.0) | 3.0 | (2.0) | 2.5 | 0.0 | 0.0 |

In calculating the content of Table 1, it is assumed that standard stop loss provisions apply, $250,000 premium cost for individual coverage with a premium of $900,000 and 125% aggregate coverage with a premium of $100,000. The result is a total premium of $1 million. In the currently disclosed embodiment, the premiums reflect a total reimbursement of $1.5 million.

As the table illustrates, the Company's coronary bypass costs were the least variable using a futures derivative in accordance with the present invention. If the Company does not hedge its risk, its total variability comprises +/−$3 million wherein if the Company elects to utilize stop loss insurance, its exposure is limited to the premiums paid ($1 million) and its potential gain is limited to the maximum reimbursement ($1.5 million).

However, by utilizing futures contracts based on a medical commodity to hedge against risks associated with healthcare costs in accordance with the present invention, the company's total variability is limited to zero, which allows the Company to better predict its future earnings.

Figure 5:
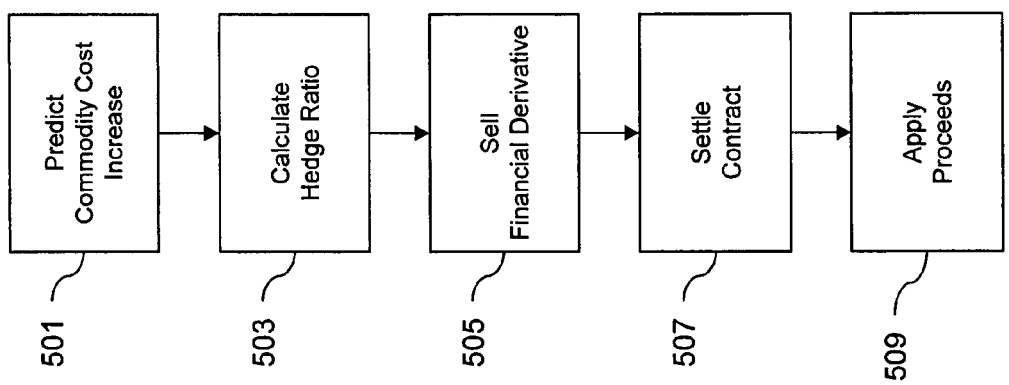
FIG. 5 is a flow chart depicting a method in which a health care provider can hedge against healthcare volatility by initially selling futures contracts with an underlying price determined by medical commodity and later settling its futures contracts.

Referring now to FIG. 5, shown is an embodiment whereby a health insurance company can hedge against healthcare cost volatility by using futures contracts based on a medical commodity in accordance with the present invention. The health insurance company predicts its expected healthcare costs for a particular medical procedure as depicted in step 501, including total revenue (premiums of $1 billion), incurred claim costs ($880 million), and administrative expenses ($80 million) for a predicted profit ($40 million). In the presently depicted embodiment, the health insurance company's worst-case scenario is that the costs incurred will be $40 million higher than predicted. Similarly, the health insurance company's best-case scenario is that its costs incurred will be $40 million less than predicted.

After predicting its costs, the health insurance company must determine the number of futures contracts it needs to sell in order to effectively hedge by calculating its hedge ratio 503 using the price of contemporaneously available commodities contracts. In this example, it is assumed that contemporaneous futures contracts are selling at $90.00, which reflects a 10% increase in the cost of performing a medical procedure (e.g., a coronary bypass) over the course of the year. Using this data as a starting point, the health insurance company decides how much risk exposure it wishes to hedge against and how much of its cash holdings it will spend to hedge that exposure. These factors are combined to form hedge ratio 503 in any manner that is known in the art. Indeed, today many entities either calculate their own hedge ratios with respect to non-healthcare risk or rely on consulting firms to help determine such ratios. Of course, other embodiments of the present invention allow for various other factors to be incorporated into a hedge ratio, as is known in the art. The hedge ratio is then used in a known manner to calculate the number of contracts to sell.

After determining the number of contracts to sell, the health insurance company would sell the requisite number of contracts as depicted in step 505. In this embodiment of the present invention, the health insurance company determines that it will sell 800 contracts at $90.00 per contract. It is also assumed that the cost of a coronary bypass is $90,000 as calculated from DRG code 127. The health insurance company can either construct custom futures contracts in the manner previously described or use a standardized futures contract, and we assume that the quantity of each contract is 10,000.

As in the previous example, the health insurance company may offer the contracts for sale privately, over the counter, or publicly on an exchange. Of course, the health insurance company can construct the contracts in any manner that it chooses, and may offer them for sale in any manner without departing from the spirit of the invention.

In this embodiment of the current invention, the margin is estimated to be $4,000,000. As previously described, the margin amount is determined by the particular exchange which is utilized for the transaction. For the purposes of this example, it is assumed that the contracts will trade on the Chicago Mercantile Exchange in a manner similar to the CPI Futures Contract which has a margin requirement of $1,250 per quarter. Because for the purposes of this example it is assumed that coronary bypass futures contracts are traded annually, an annual margin value of $5,000 per contract applies. Since 800 contracts are involved, the annual margin value for this transaction is calculated to be $4,000,000.

After offering the contacts for sale, the health insurance company can allow the contracts to settle as shown in step 507. Alternatively, it can manage the futures contracts in any manner known, including repurchasing any portion of the contracts it has offered on any day, or sell additional contracts at the market price.

On the settlement date of the futures contracts, the health insurance company delivers its contracts. The cost of the medical procedure on the settlement date is used to determine the settlement price. In the currently described embodiment, it is assumed that on the settlement date the healthcare cost of the procedure increased to $103,500. The contract value is then determined by the below formula:

100−(100*((Commodity cost on settlement date/commodity cost on offer date)−1))

Knowing that the cost of the commodity at settlement is $103,500 and the value of the procedure at offering was $90,000, the contract value is $85.00.

To determine its total profit or loss, the health insurance company uses the formula:

Units/contract*# of contracts*price difference=Profit (Loss)

In the presently described embodiment the health insurance company would profit in the amount $40,000,000. Note that when implementing the formula, the number of contracts is expressed as a negative number to indicate that the health insurance company sold them (i.e., if the health insurance company had purchased the contracts, the value would be reflected as a positive number).

In the presently described embodiment, the cost of a coronary bypass rose above the expected threshold of 10%. The actual percentage increase can be determined by using the below formula:

(Procedure Cost at Settlement/Procedure Cost at Offering)/Procedure Cost at offering))*100%

In the presently described embodiment, the cost of a coronary bypass increased 15.00%. Because the volatility was higher than expected, the health insurance company's yearly cost predictions were too low. To properly hedge against its erroneous predictions, the health insurance company applies the proceeds 509 from the sale of the contracts (e.g., $40 million) to the increased cost of healthcare. In the presently described embodiment, the health insurance company has perfectly hedged against variability as calculated by the difference between the increase in predicted healthcare costs and the monies earned on the futures contract. The health insurance company incurred no net losses However, without hedging in accordance with the present invention, the health insurance company would have incurred a net loss of $40 million.

Table 2 illustrates the benefits to the health insurance company of hedging risk utilizing a financial derivative based on the futures contract in accordance with the present invention:

TABLE 2

Hedging Comparison

| Health insurance company | Base Case No Hedge | Futures |
|---|---|---|
| Budget Projection | | |
| 2005 Insured Premium (in $millions) | 1,000 | 1,000 |
| Claims Incurred 2004 | 800 | 800 |
| Expected Trend 2004-2005 | 10% | 10% |
| Expected Claims 2005 | 880 | 880 |
| Admin Expense 2005 | 80 | 80 |
| Expected Total Costs 2005 | 960 | 960 |
| Net Expected Profit (Excluding any reimbursement or cost from hedge) | 40 | 40 |

| Actual Experience | Low Trend | High Trend | Low Trend | High Trend |
|---|---|---|---|---|
| Actual Trend 2004-2005 | 5% | 15% | 5% | 15% |
| Actual Claims 2005 (in $millions) | 840 | 920 | 840 | 920 |
| Settlement of Hedge | — | — | 40 | (40) |
| Actual Net Costs | 920 | 1,000 | 960 | 960 |
| Actual Net Surplus | 80 | 0 | 40 | 40 |
| Difference From Expected (in $millions) | (40) | 40 | 0 | 0 |

As the table illustrates, the health insurance company incurs the least variability using a futures derivative in accordance with the present invention. If the health insurance company does not hedge its risk, the total variability comprises +/-$40 million. However, by utilizing a futures contract, the health insurance company's total variability is eliminated. Using futures contracts represents the smallest variability, which allows the health insurance company to better predict its future earnings.

Figure 6:
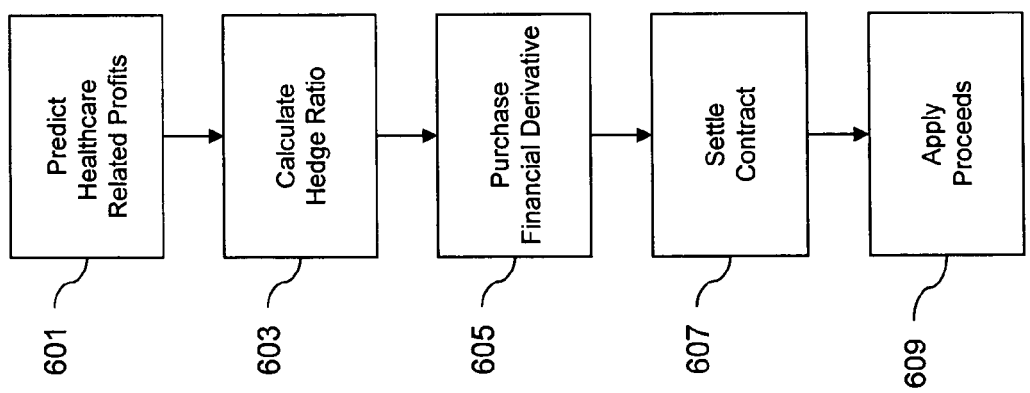
FIG. 6 is a flow chart depicting a method in which a hospital can hedge against healthcare volatility by initially purchasing futures contracts with an underlying price determined by a tangible medical commodity and later settling its futures contracts.

Referring now to FIG. 6, shown is an embodiment of the present invention wherein a hospital can manage the risks associated with healthcare cost volatility by purchasing tangible futures contracts based on medical procedures. As in the previous examples, the hospital first predicts its expected healthcare revenue for a medical procedure as depicted in step 601. For the purposes of this example, assumptions include total revenue of $19.8 million (assuming 220 procedures at $90,000 per procedure) and total expenses of $14.9 million (salaries, equipment, administrative, etc.) for a predicted profit of $4.9 million. In the example, the hospital's worst-case scenario is that the revenue generated will be $1.1 million lower than predicted. Similarly, the hospital's best-case scenario is that its revenues will be $0.2 million more than predicted.

After predicting its revenues, the hospital determines the number of futures contracts it needs to purchase in order to effectively hedge by calculating its hedge ratio 603 using the price of contemporaneously available futures contracts based on the particular medical procedure (i.e., DRG 127 coronary bypass). As in the previous example, it is assumed that contemporaneous futures contracts are trading at $90.00, which reflects a 10% increase in the cost of a coronary bypass over the course of the year. Again, using this data as a starting point, the hospital decides how much risk exposure it wishes to hedge against by forming a hedge ratio in any manner that is well known in the art to calculate the number of futures contracts to purchase.

After determining the appropriate number of contracts to purchase, the hospital would purchase the requisite number of contracts 605. In this example of the embodiment of the present invention, we assume that the hospital determines that it will purchase 19.8 contracts at $90.00 per contract. It is also assumed that the cost of a coronary bypass is $90,000 and that the quantity of each contract is 10,000.

As in the previous example, the hospital may purchase the futures contracts privately, over the counter, or publicly on an exchange.

After purchasing the contacts the hospital can allow the contracts to settle as shown in step 607 or it can manage the futures contracts in any manner known or previously described.

On the settlement date of the futures contracts, the hospital accepts its contracts. The cost of a medical procedure on the settlement date is used to determine the settlement price. In the currently described embodiment, it is assumed that on the settlement date the cost of a coronary bypass increased to $94,500. The contract value is then determined by the below formula:

100−(100*((Procedure Cost on settlement date/Procedure Cost on offer date)−1))

Knowing that the cost of a coronary bypass at settlement is $94,500 and the cost of a coronary bypass at offering was $90,000, the contract value is $95.00.

To determine its total profit or loss, the hospital uses the formula:

Units/contract*# of contracts*price difference=Profit (Loss)

In this case the hospital would gain $1.0 million. In this example, the healthcare index did not rise above the expected threshold of 10%. The actual percentage increase can be determined by using the below formula:

((Commodity Price at Settlement/Commodity Price at Offering)/Commodity Price at offering))*100% which yields 5.00%. Because the volatility was lower than the hospital's yearly revenue predictions were too high. To properly hedge against its erroneous predictions, the hospital applies the proceeds 609 from the purchase of the contracts (e.g., $1.0 million) to the decreased revenue. In the presently described embodiment, the hospital has a net loss of $100,000, the difference between the decrease in predicted revenue ($1.1 million) and the monies earned on the futures contract. While the hospital incurred a net loss of $100,000, without hedging in accordance with the present invention, the hospital would have incurred a net loss of $1.1 million.

Table 3 further illustrates the benefits to the hospital of hedging risk utilizing a financial derivative based on the medical procedure in accordance with the present invention:

TABLE 3

Hedging Comparison

| Hospital | Base Case No Hedge | Futures |
|---|---|---|
| Budget Projection | | |
| DRG 127 Capacity | 300 | 300 |
| # of DRG 127s performed in 2004 | 200 | 200 |
| Expected Trend 2004-2005 | 10% | 10% |
| Expected average number of DRG 127s performed in 2005 | 220 | 220 |
| Expected Revenue 2005 | 19.8 | 19.8 |
| Expected Total Costs 2005 | 14.9 | 14.9 |
| Net Expected Surplus (Excluding any reimbursement or cost from hedge) | 4.9 | 4.9 |

| Actual Experience | Low Trend | High Trend | Low Trend | High Trend |
|---|---|---|---|---|
| Actual Trend 2004-2005 | 5% | 15% | 5% | 15% |
| Actual average number of occupied beds in 2005 (in $millions) | 220 | 220 | 220 | 220 |
| Settlement of Hedge | — | — | 1.0 | (1.0) |
| Actual Net Revenue | 18.7 | 20.0 | 19.7 | 19.0 |
| Actual Net Surplus | 4.8 | 5.1 | 4.8 | 4.1 |
| Difference From Expected (in $millions) | (0.2) | 0.1 | (0.1) | (0.8) |

As the table illustrates, the hospital has the least downside potential using a futures derivative in accordance with the present invention. If the hospital chose not to hedge its risk, the total downside potential is $0.2 million. However, by utilizing a futures contract based on a healthcare index to hedge against risks associated with healthcare costs, the hospital's downside potential is limited to $150,000.

The present invention also contemplates a security product that is similar in structure to a debt obligation. Because of regional and facility variations in both the cost and quality of healthcare, financial derivative contracts may not be feasible for each party. In short, some entities that would otherwise be participants in such a market could be effectively precluded from buying and selling financial derivatives.

The present invention allows these parties to construct a debt like instrument wherein the seller could offer a percentage of its medical service capacity in exchange for much needed capital before the service is actually performed. Advantageously, the seller can select the rate of return similar to a coupon in a coupon bond. In addition, it can be underwritten by any well known underwriter to reduce the risk of such an offering. Also, many private hospitals already offer general bonds that are rated by Moody's and other ratings agencies, so the risk involved in such an offering is easily ascertained. This improves the communication between potential buyers and sellers, and improves market efficiency overall.

However, the principal advantage of this instrument is that it takes advantage of the inherent cost of capital spread between potential sellers and potential buyers.

Typical buyers of such a product include large corporations, institutional investors, and the government. The cost of capital for these entities is roughly equivalent to the entity's weighted average cost of capital, which is a function of the cost to issue corporate debt and the cost to issue corporate equity, plus the value of cost certainty. For entities of this magnitude, the cost of corporate debt is approximately 5%, the cost to issue debit is approximately 15%, and the weighted average cost of capital is approximately 10%. The value of certainty is dependent upon the inherent volatility that the entity needs to hedge against. This range is typically at least 1% for a volatile instrument. As a result, an entity of this type pays approximately 4% to borrow funds. However, the growth rate of healthcare is approximately 10% per year. In addition, the growth rates are highly volatile. Accordingly, if a security product was offered that allowed the pre-purchase of healthcare products, it would be economically beneficial for a purchaser to pre-purchase at least a portion of its expected expenditures because the cost to borrow the requisite funds and prepay for the healthcare product is less than the inherent increase associated with both the direct healthcare related costs and the indirect expense of healthcare cost control practices.

In addition, typical sellers of such a product have a higher cost of capital than the entities that wish to purchase them. For example, many healthcare providers typically have costs of capital that exceed 6%. As a result, healthcare providers have historically had less access to capital. By offering the security product of the present invention, healthcare providers have access to capital at rates that are markedly lower than currently available.

Turning now to FIG. 7, depicted is the analysis and process by which a large self insurer, such as General Motors would purchase a security product based upon commoditized medical products. Initially, the self insurer estimates the number of medical procedures that it will incur 701. In this example, the estimated number of procedures is determined by utilizing detailed internal records of their covered population. Of course, any other method for estimating the number of procedures that will be incurred can be utilized in accordance with the present invention.

Next, the total cost of the expenditures is estimated 703. In this example, total costs are estimated by multiplying the estimated number of required procedures as determined by forward looking estimates as derived in step 701 by its average cost as determined by historically negotiated costs and summing the results. Of course, any other method can be utilized without departing from the scope of the invention.

After estimating the total cost of medical procedures 703, the large self insurer calculates a hedge ratio 705 to determine the number of procedures to pre-purchase. A hedge ratio is determined in any well known manner. In the present example, the hedge ratio is 25% (i.e., the self insurer has determined that it will pre-purchase 25% of its expected procedures).

After determining the number of procedures to pre-purchase 705, the large self insurer calculates the initial outlays of the pre-purchased procedures 707. In this example, the estimated number of procedures is multiplied by the hedge ratio to determine the estimated number of securities to purchase. To calculate the fair market value of these securities, the entity discounts the security the procedure's expected cost increase and its cost of capital. In this example, the expected cost increase for each procedure is assumed to be 10% and the entity's cost of capital is estimated to be 5%. To calculate the total initial outlays, the initial outlays for each medical procedure are summed.

Of course, the entity will have to pay the full market value of any procedure that it did not pre-purchase as shown in 709. The eventual outlay for the remaining needed procedures is determined by multiplying the number of remaining procedures (in this case 75%) by the expected actual average cost per procedure adjusted for any expected cost increase. Each individual procedure's outlay is summed to determine the final eventual outlay required.

Table 4 below highlights the advantages to hedging with a security product in accordance with the present invention.

TABLE 4

Security Product Hedging

|  | DOWN TREND | EXPECTED | UPTREND |
|---|---|---|---|
| Large Employer Cost Model | No pre-purchasing | No pre-purchasing | No pre-purchasing |
| Actual Cost Increase | 5% | 10% | 15% |
| Upfront Pre-Payment (6 Procedures) | 0 | 0 | 0 |
| Financing Costs | 0 | 0 | 0 |
| Payment After Procedure | 215,831,127 | 226,108,800 | 236,386,473 |
| (6 Procedures) Total Costs | 215,831,127 | 226,108,800 | 236,386,473 |
| % change from Expected, No Pre Purchasing | −4.5% | 0% | 4.5% |
|  | 25% of Procedures pre-purchased | 25% of Procedures pre-purchased | 25% of Procedures pre-purchased |
| Actual Cost Increase | 5% | 10% | 15% |
| Upfront Pre-Payment (6 Procedures) | 53,957,782 | 53,957,782 | 53,957,782 |
| Financing Costs | 2,697,889 | 2,697,889 | 2,697,889 |
| Payment After Procedure | 161,873,345 | 169,581,600 | 177,289,855 |
| (6 Procedures) Total Costs | 218,529,016 | 226,237,271 | 233,945,525 |
| % change from Expected, Pre Purchasing | −3.4% | 0.1% | 3.5% |

The preceding table assumes that in the best case scenario, the increased costs of medical procedures will be only 5% and in the worst case the actual cost increases will be 15%. The financing costs are assumed to simply be the interest charges at the large self insurers at it's cost of capital on the up front pre-purchases.

As can be seen from the table, the volatility is minimized when the entity pre-purchases securities in accordance with the present invention. Without purchasing medical product securities, total volatility is +/−4.5%. In contrast, the volatility of the large self insurer is only +/−3.5% which allows the large self insurer to better predict its future earnings.

Referring to FIG. 8, depicted is the analysis and process by which a large healthcare provider would offer a security product based upon commoditized medical products. Initially, the healthcare provider estimates the number of medical procedures that it will perform 801. In this example, the estimated number of procedures is determined by utilizing detailed internal records of their facilities. Of course, any other method for estimating the number of procedures that will be incurred can be utilized in accordance with the present invention.

Next, the total price of the service is estimated 803. In this example, total prices are estimated by multiplying the estimated number of required procedures as determined by forward looking estimates as derived in step 801 by the average historically negotiated price and summing the results. Of course, any other method can be utilized without departing from the scope of the invention.

After estimating the total price of medical procedures 803, the healthcare provider calculates a hedge ratio 805 to determine the number of procedures to offer (i.e., "pre-sell"). A hedge ratio is determined in any well known manner. In the present example, the hedge ratio is 25% (i.e., the healthcare provider has determined that it will pre-sell 25% of its expected procedures).

After determining the number of procedures to pre-sell 805, the healthcare provider calculates the initial inflows of the pre-sold procedures 807. In this example, the estimated number of procedures is multiplied by the hedge ratio to determine the estimated number of securities to sell. To calculate the fair market value of these securities, the entity discounts the security the procedure's expected cost increase and its cost of capital. In this example, the expected cost increase for each procedure is assumed to be 10% and the entity's cost of capital is estimated to be 5%. To calculate the total initial inflows, the initial inflows for each medical procedure are summed.

Of course, the entity will have to sell the full market value of any procedure that it did not pre-sell as shown in 809. The eventual inflow for the remaining procedures is determined by multiplying the number of remaining procedures (in this case 75%) by the expected actual average cost per procedure adjusted for any expected cost increase. Each individual procedure's inflow is summed to determine the final eventual net inflow.

Table 5 below highlights the advantages to hedging with a security product in accordance with the present invention.

TABLE 5

Security Product Hedging

|  | DOWN TREND | EXPECTED | UP TREND |
|---|---|---|---|
| Provider Cost Model | No pre-selling | No pre-selling | No pre-selling |
| Actual Cost Increase | 5% | 10% | 15% |
| Cost to Issue Bonds ($5/$1,000) | 0 | 0 | 0 |
| Upfront Revenue (6 Procedures) | 0 | 0 | 0 |
| Reduced Working Capital Expense | 0 | 0 | 0 |
| Revenue After Service | 71,943,709 | 75,369,600 | 78,795,491 |
| (6 Procedures) |  |  |  |
| Net Revenue | 71,943,709 | 75,369,600 | 78,795,491 |
| Delivery Costs (assumes 75% COGS) | 53,957,782 | 56,527,200 | 59,096,618 |
| Reduced Working Capital Expense | 0 | 0 | 0 |
| Net Income | 17,985,927 | 18,842,400 | 19,698,873 |
| % change from Expected, No Pre Selling | −4.5% | 0% | 4.5% |
|  | 25% of Procedure Capacity presold | 25% of Procedure Capacity presold | 25% of Procedure Capacity presold |
| Actual Price Increase | 5% | 10% | 15% |
| Cost to Issue Bonds ($5/$1,000) | −89,930 | −89,930 | −89,930 |
| Upfront Pre-Payment (6 Procedures) | 17,985,927 | 17,985,927 | 17,985,927 |
| Revenue After Service | 53,957,782 | 56,527,200 | 59,096,618 |
| (6 Procedures) |  |  |  |
| Net Revenue | 71,853,779 | 74,423,198 | 76,992,616 |
| Delivery Costs (assumes 75% COGS) | 53,957,782 | 56,527,200 | 59,096,618 |
| Reduced Working Capital Expense | −1,073,760 | −1,073,760 | −1,073,760 |
| Net Income | 18,969,757 | 18,969,757 | 18,969,757 |
| % change from Expected, Pre Selling | 0.7% | 0.7% | 0.7% |

The preceding table assumes that in the best case scenario, the increased costs of medical procedures will be only 5% and in the worst case the actual cost increases will be 15%. The financing costs are assumed to simply be 0.5% of the value of the issued securities. In addition, it is assumed that the large healthcare provider has an operating margin of 25%.

As can be seen from the table, the volatility is minimized when the entity pre-sells securities in accordance with the present invention. Without pre-selling medical product securities, total volatility is +/−4.5%. In contrast, the volatility of the large self insurer is only 0.7% which allows the large self insurer to better predict its future earnings. In addition, the healthcare provider earns at least a portion of the capital for its services up front. This capital can be used to service existing debt, invest in other securities, or make other capital expenditures. As a result, the healthcare provider is afforded greater cash flow and liquidity.

What is claimed is:

1. A method of managing the costs of a medical procedure, medical service or medical product comprising the steps of:
   storing, via a storage device, information regarding a plurality of estimated healthcare related expenses for a predetermined future time period, wherein said plurality of estimated healthcare related expenses are expenses for a number of medical procedures expected to be incurred by a buyer at said predetermined future time period, expenses for a number of medical services expected to be incurred by said buyer at said predetermined future time period, or expenses for a number of medical products expected to be incurred by said buyer for said predetermined future time period, wherein said plurality of healthcare related expenses are stored in a storage device of or associated with the buyer of said healthcare services;
   determining, via a computer processor, information regarding an expected demand for each of said medical procedure, said medical services, and said medical products at said future time period by utilizing at least one medical code, wherein said information regarding said expected demand is calculated in part based on historical information regarding health transactions of a plurality of buyers of healthcare services and a plurality of suppliers of healthcare services;
   determining, via said computer processor, an expected change of costs in said medical procedure, said medical service, or said medical product during said predetermined future period of time based on said estimated healthcare related expenses and said determined expected demand;

calculating, via said computer processor, a hedge ratio based on said determined expected change of costs in said medical procedure, said medical service, or said medical product during said predetermined future period of time, wherein said hedge ratio is a ratio calculated to mitigate deviations in said plurality of estimated healthcare related expenses and;

determining, via said computer processor, a quantity of a healthcare derivative instrument to purchase from said hedge ratio, wherein said healthcare derivative instrument is related to a commodity based on the healthcare related expenses, wherein said healthcare derivative instrument comprises a rate of return, a duration and settlement terms, wherein a price of said healthcare derivative instrument is a function of a price of said at least one medical code representing at least one of said medical procedure, said medical service, or said medical product, and wherein said rate or return of said healthcare derivative instrument is a function of an average cost of said medical procedure, said medical service, or said medical product, and wherein said rate of return fluctuates from a purchase date to a future time period as said average cost of said medical procedure, medical service or medical product fluctuates from said purchase date to said future time period purchasing, via said computer processor, said determined quantity of said healthcare derivative instrument at a first time period, wherein said determined quantity of said healthcare derivative instrument authorizes said buyer to purchase said number of medical procedures, said number of medical services, or said number of medical products at said predetermined future time period;

purchasing, via said computer processor, said quantity of said number of medical procedures, said number of medical services, or said number of medical products at predetermined said future time period, wherein a price associated with said number of medical procedures, a price associated with said number of medical services, or a price associated with said number of medical products at said predetermined future time period fluctuates between said first time period and said predetermined future time period.

2. A method according to claim 1 wherein said healthcare derivative instrument further comprises a duration of time equal to said predetermined period of time.

3. A method according to claim 1 wherein said step of purchasing said healthcare derivative instrument occurs at the beginning of said predetermined period of time.

4. A method according to claim 1 wherein said healthcare derivative instrument further comprises a settlement date.

5. A method according to claim 4 wherein said settlement date occurs at the end of said predetermined future period of time.

6. A method according to claim 5 wherein said step of purchasing said quantity of said number of medical procedures, said number of medical services, or said number of medical products occurs after said settlement date of said healthcare derivative instrument.

7. A method according to claim 1 further comprising the step of purchasing a second quantity of said healthcare derivative instrument.

8. A method according to claim 7 wherein said second quantity of said healthcare derivative instrument further comprises a price determined by the market of said medical procedure, medical service, or medical product.

9. The method of claim 1 wherein said healthcare derivative instrument comprises at least one selected from the group consisting of a futures contract, an option, a financial security, and a futures option.

10. A method of managing the revenue of a medical procedure, medical service or medical product comprising the steps of:

predicting, via a computer processor, the expected capacity for a medical procedure, medical service or medical product for a predetermined future period of time;

determining, via said computer processor, information regarding an expected demand for each of said medical procedure, said medical services, and said medical product at said predetermined future period of time by utilizing at least one medical code, wherein said information regarding said expected demand is calculated in part based on historical information regarding health transactions of a plurality of buyers of healthcare services and a plurality of suppliers of healthcare services;

determining, via said computer processor, an expected change of revenues from said medical procedure, said medical service, or said medical product at said predetermined future period of time based on said predicted capacity and said determined expected demand;

calculating, via a computer processor, a hedge ratio based on said determined expected change of revenues in said medical procedure, said medical service, or said medical product during said predetermined future period of time, wherein said hedge ratio is a ratio calculated to mitigate deviations in said revenue from said medical procedure, said medical service or said medical product at said predetermined future period of time, and further wherein the hedge ratio is used to determine a quantity of a healthcare derivative instrument to sell, at a current period of time, wherein the current period of time precedes the predetermined future period of time, and wherein the healthcare derivative instrument is related to a commodity based on said medical procedure, said medical service or said medical product, wherein said healthcare derivative instrument comprises a rate of return, a duration and settlement terms, wherein a price of said healthcare derivative instrument is a function of a price of said at least one medical code representing at least one of said medical procedure, said medical service, or said medical product, and wherein said rate or return of said healthcare derivative instrument is a function of an average expected market value of said medical procedure, said medical service, or said medical product, and wherein said rate of return fluctuates from said current period of time to a predetermined future period of time as said average expected market value of said medical procedure, medical service or medical product fluctuates from said current period of time to said predetermined future period of time;

determining, via the computer processor, a quantity of a financial instrument to offer for sale from the calculated hedge ratio;

wherein said financial instrument is related to said medical procedure, medical service, or medical product;

offering, via a computer, said determined quantity of said financial instrument to a party; and selling, via the computer, said determined quantity of said financial instrument.

11. A method according to claim 10 wherein said financial instrument further comprises a duration of time equal to said predetermined period of time.

12. A method according to claim 10 wherein said step of selling said financial instrument occurs at the beginning of said predetermined period of time.

13. A method according to claim 10 wherein said financial instrument further comprises a settlement date.

14. A method according to claim 13 wherein said settlement date occurs at the end of said predetermined future period of time.

15. A method according to claim 13 wherein said step of selling a quantity of said financial instrument occurs before said settlement date of said derivative instrument.

16. A method according to claim 10 further comprising the step of offering a second quantity of said financial instrument.

17. A method according to claim 16 wherein said second quantity of said financial instrument further comprises a price determined by said medical procedure, medical service, or medical product.

18. The method of claim 10 wherein said financial instrument comprises at least one selected from the group consisting of a futures contract, an option, a financial security, and a futures option.

19. The method of claim 1 wherein said hedge ratio utilizes a price of an existing futures contract as a price source.

20. The method of claim 10, wherein said financial instrument comprises at least one selected from the group consisting of a futures contract, an option, a financial security, and a futures option.

* * * * *

UNITED STATES PATENT AND TRADEMARK OFFICE
CERTIFICATE OF CORRECTION

PATENT NO. : 7,801,786 B2  
APPLICATION NO. : 11/324031  
DATED : September 21, 2010  
INVENTOR(S) : Thomas Leonard Smith, Marshall Howard Hudes and James Mark Staba It is certified that error appears in the above-identified patent and that said Letters Patent is hereby corrected as shown below:

On the Title Page, item (54) and in the Specification, Column 1, line 2, in the title of the invention, replace "commodoties" with --commodities--

Signed and Sealed this
Fourth Day of February, 2014

Michelle K. Lee
*Deputy Director of the United States Patent and Trademark Office*